United States Patent [19]

Demko

[11] Patent Number: 5,240,939
[45] Date of Patent: Aug. 31, 1993

[54] NITROGEN BRIDGE TETRAHYDROISOQUINOLINES

[75] Inventor: Donald M. Demko, Palmer Township, Northhampton County, Pa.

[73] Assignee: Anaquest, Inc., Liberty Corner, N.J.

[21] Appl. No.: 977,311

[22] Filed: Nov. 16, 1992

Related U.S. Application Data

[63] Continuation-in-part of Ser. No. 785,958, Oct. 31, 1991, abandoned.

[51] Int. Cl.$^5$ .................... A61K 31/47; C07C 401/14
[52] U.S. Cl. ................................ 514/308; 546/140
[58] Field of Search ................. 546/140; 514/308

[56] References Cited

U.S. PATENT DOCUMENTS

| | | | |
|---|---|---|---|
| 3,004,031 | 10/1961 | Taylor et al. | 546/140 |
| 4,179,507 | 12/1979 | Stenlake et al. | 514/308 |
| 4,192,877 | 3/1980 | Savarese et al. | 514/308 |
| 4,235,906 | 1/1980 | Savarese et al. | 514/308 |
| 4,701,460 | 10/1987 | El-Sayad et al. | 546/140 |
| 4,761,418 | 8/1988 | Swaringen, Jr. et al. | 514/308 |

Primary Examiner—C. Warren Ivy
Assistant Examiner—Zinna N. Davis
Attorney, Agent, or Firm—R. Hain Swope; Larry R. Cassett

[57] ABSTRACT

Muscle relaxant nitrogen bridge tetrahydroisoquinolines are disclosed. The novel compounds are represented by the formula

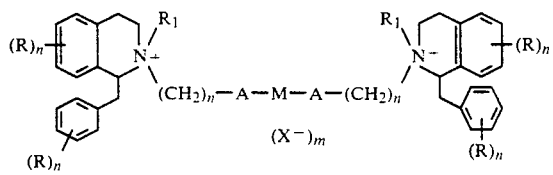

wherein A is

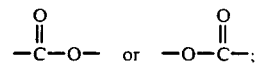

M represents —(CH$_2$)$_n$—Z—(CH$_2$)$_n$ or

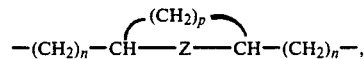

R is a C$_{1-3}$ alkoxy group, or adjacent Rs are a methylenedioxy group, R$_1$ is lower alkyl; n is 1-6; m is 2 or 3; p is 1-3; Z is —N$^+$(R$_2$R$_3$)—, —N(R$_4$)—,

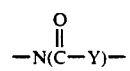

and —N[(CH$_2$)$_n$—A—R$_5$]—; R$_2$ and R$_3$ are independently lower alkyl groups wherein a carbon atom within the chain may be replaced by a heteroatom, lower cycloalkyl, lower cycloalkyl lower alkyl, aryl, aryl lower alkyl, a 4- to 6-member heteroring or may be combined with the nitrogen to form a heteroring; R$_4$ is a straight- or branched- chain C$_{1-10}$ alkyl wherein a carbon atom within the chain may be replaced by a heteroatom, lower cycloalkyl, lower cycloalkyl lower alkyl, aryl, or a heteroring, which groups may be substituted or unsubstituted; or

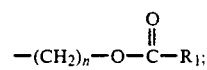

R$_5$ is lower alkyl or lower alkenyl; Y is hydrogen, lower alkyl wherein a carbon atom within the chain may be replaced by a heteroatom, lower alkoxy, aryl, aryloxy, lower cycloalkyl, lower cycloalkyl lower alkyl, a 4- to 6-member heteroring or —NR$_2$R$_3$; X$^-$ is a pharmaceutically acceptable anion, and optically active forms thereof, meso forms thereof, cis-trans isomeric forms thereof and racemates thereof.

17 Claims, No Drawings

NITROGEN BRIDGE TETRAHYDROISOQUINOLINES

RELATED APPLICATIONS

This application is a continuation-in-part of U.S. patent application Ser. No. 07/785,958, filed Oct. 31, 1991 now abandoned.

This invention relates to novel bis-tetrahydroisoquinolines linked by a bridge containing two ester linkages and a nitrogen atom, preferably a quaternary nitrogen. These compounds are muscle relaxants possessing advantageous properties.

BACKGROUND OF THE INVENTION

Bis-1-benzyl-tetrahydroisoquinolines, generally represented by the structure

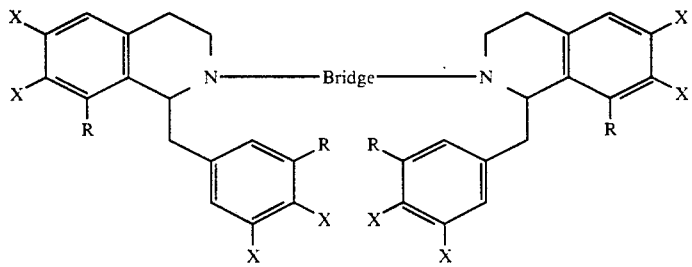

are an art-recognized class of compounds. In the above formula, X typically represents hydrogen or lower alkoxy, such as methoxy, and R is hydrogen, lower alkoxy or lower alkyl. In certain instances, the nitrogen can be a quaternary nitrogen.

The linking structure represented by "Bridge" in the above formula can be a methylene link as in the early muscle relaxant laudexium which has the structure

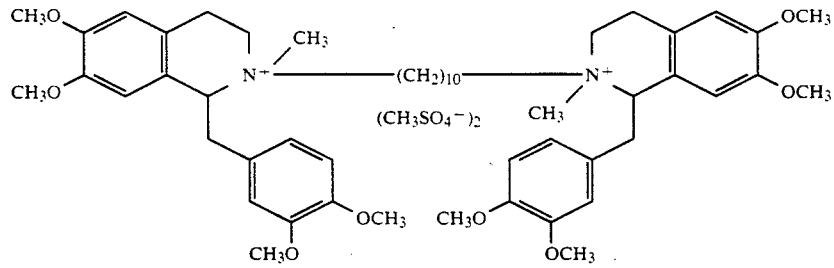

In later compounds of this group, the bridge is, in general, a carbon-oxygen structure which typically contains ester linkages. In Taylor et al, U.S. Pat. No. 3,004,031, issued Oct. 10, 1961, the bridge is —(CH$_2$)$_m$—O.CO—(CH$_2$)$_n$—CO.O—(CH$_2$)$_m$— wherein m is 2 or 3, and n is 0–4. El-Sayad et al, U.S. Pat. No. 4,701,460, issued Oct. 20, 1987, disclose a similar bridge wherein m is 3 and n is 2. The structure of the commercial muscle relaxant atracurium is as given above for laudexium with the exception that the bridge is

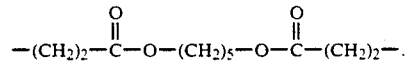

In Stenlake et al, U.S. Pat. No. 4,179,507, issued Dec. 18, 1979, the bridge is defined as A.CO.O.L.O.CO.B—, wherein A and B are 1–3 carbon alkylene chains, L is a 2–12 carbon alkylene chain or —R—O—R— where each R has at least two carbon atoms, and their total does not exceed 11 carbon atoms.

Savarese et al, U.S. Pat. Nos. 4,192,877, issued Mar. 11, 1980 and 4,235,906, issued Nov. 25, 1980, disclose compounds of the above general formula wherein the bridge is

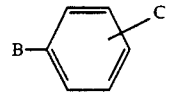

B and C or either ortho or para and are

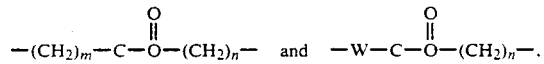

respectfully, with W being —CH$_2$— or CH=CH—.

Swaringen, Jr. et al, U.S. Pat. No. 4,761,418, issued Aug. 2, 1988, disclose compounds of the above formula wherein the bridge is

The compounds described in the above-referenced patents are, in general, neuromuscular blocking agents which produce skeletal muscle relaxation in mammals, including man.

Certain compounds belonging to a second art-recognized group have been found to possess muscle relaxing activity. These are linear tri-, tetra-, penta- and hexaonium compounds such as those represented by the formulae

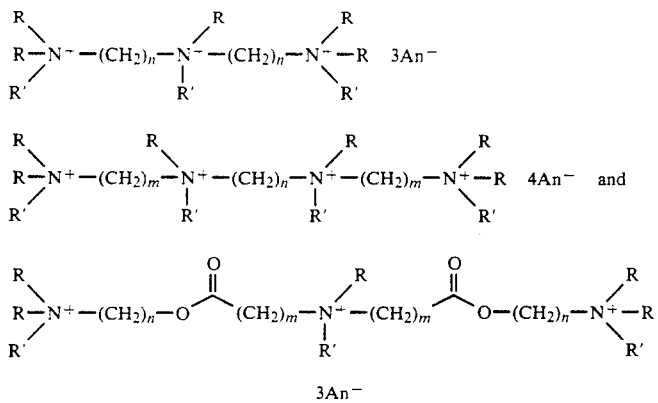

wherein R and R' are alkyl groups and may be the same or different, m and n are generally 1 to 3, and An⁻ represents an anion.

There had been over the years a quest for skeletal muscle relaxants of ever-increasing potency. This was based primarily on the philosophy that it is advantageous to use smaller and smaller quantities of a compound to elicit a given therapeutic response since the incidence or severity of side effects would be correspondingly reduced. More recently, however, it has been realized that increases in potency were usually accompanied by delays in onset of activity and duration of activity once begun. Accordingly, what is sought are compounds having a balance of properties, i.e. adequate potency in combination with a rapid onset of activity, comparatively short duration of activity, a good recovery, and an advantageous cardiovascular picture. Such compounds are provided in accordance with the present invention.

SUMMARY OF THE INVENTION

In accordance with the present invention, there are provided bis-tetrahydroisoquinoline compounds represented by the general formula

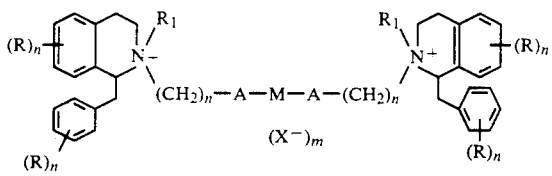

wherein A is

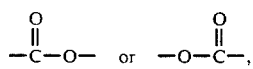

M is —(CH$_2$)$_n$—Z—(CH$_2$)$_n$— or

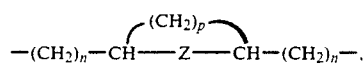

Z is a tertiary or quaternary nitrogen, R represents a C$_{1-3}$ alkoxy group or adjacent Rs are a methylenedioxy group, R$_1$ is a lower alkyl group, n is 1-6, m is 2 or 3, P is 1 to 3 and X⁻ is a pharmaceutically acceptable anion.

DETAILED DESCRIPTION OF THE INVENTION

The novel bis-tetrahydrorisoquinoline compounds of the present invention possess very desirable muscle relaxant properties.

In general, neuromuscular blocking agents are of two types, non-depolarizing and depolarizing. Examples of nondepolarizing muscle relaxants include d-tubocurarine, pancuronium gallamine, atracurium, diallyltoxiferine and toxiferine. Examples of depolarizing neuromuscular blocking agents include succinylcholine and decamethonium.

In general, the nondepolarizing muscle relaxants possess a long duration of action, e.g. from one up to three hours. This can be a decided disadvantage for surgical procedures requiring less than one hour because, at the end of the procedure, it may be necessary to continue assisting the patient's breathing until he or she has fully recovered from the effects of the drug. Nondepolarizing muscle relaxants are likewise known to have side effects, such as tachycardia and hypertension.

While nondepolarizing agents can be antagonized with compounds having antcholinesterase activity, the antagonists themselves typically produce side effects which may be counteracted with an anticholinergic agent such as atropine. Therefore, a second, and perhaps a third, therapeutic agent must be administered to the patient.

Depolarizing neuromuscular blocking agents as a class are recognized as being nonreversible. In certain instances, they can cause side effects such as intraocular pressure, intragastric tension, cardiac arrhythmias, potassium release, and muscle pain. They are also appreciably shorter in duration of action than the nondepolarizing agents.

The nondepolarizing neuromuscular blocking agents of this invention are advantageous in that they have an exceptional balance of properties which make them useful as muscle relaxants for surgical procedures of any duration, particularly short term procedures. The subject compounds are characterized by a rapid onset of activity, short duration of activity, rapid recovery, and minimal cardiovascular effects. They are suitable for use in surgical procedures of any duration, but particularly short term procedures, i.e. those of thirty minutes and below, such as intubation of the trachea.

The novel bis-tetrahydrorisoquinoline compounds of the present invention are represented by the formula

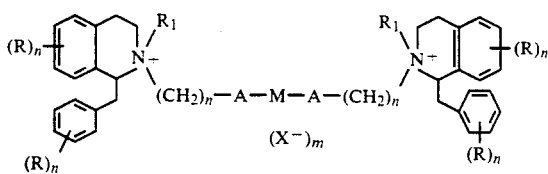

wherein:
A represents

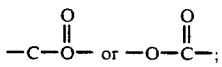

M is —(CH$_2$)$_n$—Z—(CH$_2$)$_n$— or

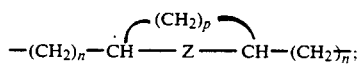

R represents a C$_{1-3}$ alkoxy group or adjacent Rs are a methylenedioxy group; R$_1$ is a lower alkyl group; Z is selected from the group consisting of —N$^+$(R$_2$R$_3$)—, —N(R$_4$)—,

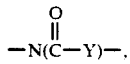

and —N[(CH$_2$)$_n$—A—R$_5$]—; R$_2$ and R$_3$ are independently selected the group consisting of: lower alkyl wherein one of the carbon atoms within the chain may be replaced by a heteroatom selected from the group consisting of N, S, and O; lower cycloalkyl; lower cycloalkyl lower alkyl; aryl; aryl lower alkyl; a 4- to 6-member heterocyclic ring; or wherein M is —(CH$_2$)$_n$—Z—(CH$_2$)$_n$—, R$_2$ and R$_3$, together with the nitrogen to which they are attached, form a 4- to 6-member heterocyclic ring.

R$_4$ is a straight- or branched-chain C$_{1-10}$ alkyl group wherein one or more of the carbon atoms within the chain may be replaced by a heteroatom selected from the group consisting of N, S, and O; a substituted or unsubstituted lower cycloalkyl group; a substituted or unsubstituted lower cycloalkyl lower alkyl group; a substituted or unsubstituted aryl group; a substituted or unsubstituted 4- to 6-member heterocyclic ring; or

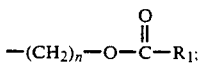

R$_5$ is lower alkyl or lower alkenyl;

Y is hydrogen, a lower alkyl wherein one or more of the carbon atoms within the chain may be replaced by a heteroatom selected from the group consisting of N, S, and O; lower alkoxy; aryl, aryl; aryloxy; lower cycloalkyl; lower cycloalkyl lower alkyl; a 4- to 6-member heterocyclic ring; or —NR$_2$R$_3$;

X$^-$ is a pharmaceutically acceptable anion;
m is 2 or 3;
n is independently 1 to 6;
p is 1 to 3, optically active forms thereof, meso forms thereof, cis-trans isomeric forms thereof and racemates thereof.

In the above Formula I, R is preferably methoxy or adjacent Rs are methylenedioxy, R$_1$ is preferably methyl or ethyl, with methyl being particularly preferred; R$_2$ and R$_3$, where they are lower alkyl, are preferably isopropyl or ethyl.

Unless otherwise defined in a particular instance, the terms "lower alkyl" or "lower alkenyl" as utilized herein, indicate straight- or branched-chain hydrocarbon groups containing from one to six carbon atoms. This definition applies as well to the alkyl portion of lower alkoxy groups unless otherwise defined. The term "lower cycloalkyl" as utilized herein indicated cyclic hydrocarbon groups containing from three to six carbon atoms. The term "halogen" refers to all four halogens with fluorine and chlorine being preferred.

In the meaning of R$_4$ and Y in the above Formula I, wherein one or more carbon atoms in an alkyl chain may be replaced with a heteroatom, nitrogen and oxygen are particularly preferred. R$_4$ may be, for example, a —(CH$_2$)$_2$—NH—(CH$_2$)$_2$—CH$_3$ group, Y may be —CH$_2$—O—C$_2$H$_5$ group, and the like.

Wherein R$_4$, Y, R$_2$, and/or R$_3$ may be a heterocyclic ring, such ring may have 4 to 6 members and may contain one or more heteroatoms selected from N, S, and O. It will be appreciated that, wherein R$_2$ and R$_3$ are combined to form a heterocyclic ring, such ring by definition must contain at least one nitrogen atom. Examples of suitable heterorings include azetidinyl, pyrrolyl, piperidyl, pyrazyl, morpholyl, pyrimidyl, triazolyl, pyrrolidinyl, indazolyl, indolyl, furanyl, thienyl, and the like. These heterorings, as well as cycloalkyl groups or aryl, e.g. phenyl, naphthyl groups, in the above Formula I may be substituted with one or more substituents preferably selected from the group consisting of lower-alkyl, halogenated lower alkyl, lower alkoxy, halogen, oxo, hydroxy, and acyloxy. Preferred heterorings include azetidinyl, pyrrolidinyl, thienyl, furanyl and piperidyl.

Pharmaceutically acceptable anions represented by X$^-$ in the above Formula I include, for example, inorganic anions such as the chloride, bromide, sulfate, phosphate, and the like, and the organic anions, such as the acetate, oxalate, trifluoroacetate, succinate, tartrate, benzene sulfonate (besylate), methane sulfonate (mesylate), toluene sulfonate (tosylate), and the like. Particularly preferred pharmaceutically acceptable anions in accordance with the present invention are the bromide, chloride and besylate.

In a preferred group of compounds according to the present invention, R in the above Formula I is methoxy, R$_1$ is methyl, n is two or three in the benzyl rings and two otherwise, Z is a quaternary nitrogen, i.e. Z is —N$^+$(R$_2$R$_3$)—, and m is three. Particularly preferred are those compounds in this group wherein one of R$_2$ and R$_3$ is lower-alkyl.

In another preferred group of compounds according to the present invention, R in the above Formula I is methoxy, R$_1$ is methyl, n is two or three in the benzyl rings and two otherwise, m is two and Z is —NC(R$_4$)— wherein R$_4$ is a lower alkyl or

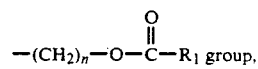

particularly t-butyl or 2-acetoxyethyl. In a further preferred group of compounds, m, n, R and R$_1$ are as defined above, and Z is

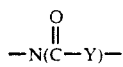

wherein Y is a aryloxy, alkoxy or hydrogen. Particularly preferred compounds in this group are those wherein Y is methoxy, benzyloxy, or hydrogen.

The compounds of the present invention can be prepared by various methods. In general, the compounds of the above Formula I can be prepared by reacting an amine diol represented by the formula

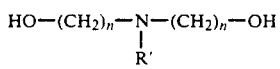

wherein n is 1 to 6, and R' is $R_2$, $R_3$ or $R_4$, as defined above, with acryloylchloride to form the corresponding bis-acrylate which is then reacted with a desired benzyl-tetrahydroisoquinoline to form a bis-amine according to the following reaction scheme:

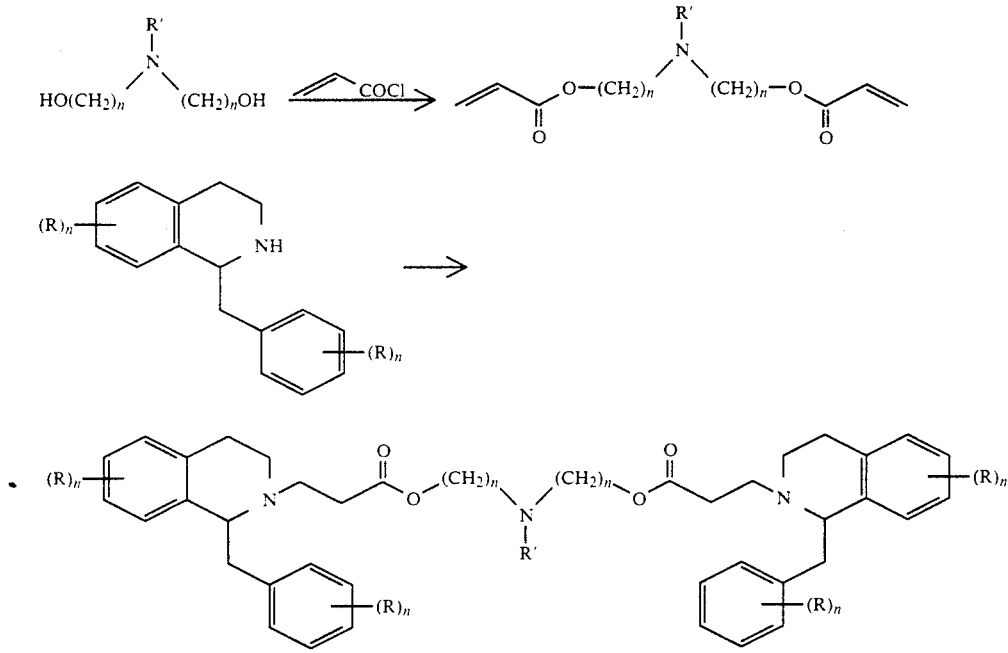

the bis-amine is then reacted with a conventional alkylating agent represented by the formula $R_1$-Hal wherein $R_1$ is as defined above, and Hal represents halogen, preferably bromide. There is formed the compound of formula I above wherein Z is $—N^+(R_2R_3)—$ and one of $R_2$ and $R_3$ is a lower alkyl. The above reaction illustrates preparation of the subject compounds, where M is $—(CH_2)_n—Z—(CH_2)_n—$ and is also applicable to those compounds where M is

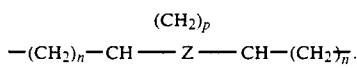

It has been found that the ring nitrogens quaternize in the above reaction prior to the bridge nitrogen. Therefore, it is possible to form those compounds of Formula I where Z is other than $—N^+(R_2R_3)—$ by controlling the reaction conditions, e.g. since the reaction proceeds more slowly with the bromide than the iodide, it is possible to stop the reaction before quaternization of the bridge nitrogen commences. It has also been found that certain substituents on the bridge nitrogen will prevent quaternization. Examples of these include t-butyl and

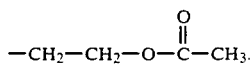

In contrast, using the iodide, e.g. $R_1$—I, the reaction is more rapid and quaternization of the bridge nitrogen readily takes place.

The above reaction scheme, reaction of the aminodiol with acryloyl chloride is carried at reduced temperatures, e.g. 0° C. to 25° C. in the presence of an organic base such as triethylamine, 4-dimethylaminopyridine, or the like. The reaction of the resulting bis-amine with the desired 1-benzyl-tetrahydroisoquinoline is carried out in the presence of a suitable organic solvent, e.g. p-xylene, tolune, and the like, at elevated temperature, e.g. 118° C. to 135° C., preferably 125° C. to 130° C. The product is typically recovered by flash chromotography.

Quaternization of the bis-amine is carried out in an organic solvent, such as acetonitrile, methylene chloride, and the like. Utilizing methyl bromide as the alkylating agent for about three days at room temperature will result in quaternization of both the ring and bridge nitrogens. Quaternization of the ring and bridge nitrogens can be effected with methyl iodide in about 24 hours.

The amine diol described above may alternately be reacted with a compound represented by the formula Hal—$(CH_2)_n$—COOH wherein n is as defined above, and Hal is halogen, preferably bromine to yield a compound represented by the formula

wherein R' is as defined above. This compound is then reacted with a desired benzyl-tetrahydroisoquinoline to form a bis-amine which is then quaternized as described above.

Alternatively, the desired 1-benzyl-tetrahydroisoquinoline is reacted with a bromo-alkanol, preferably in an organic solvent, such as acetonitrile or methylene chloride, with mild heating, e.g. about 50° C., to form the corresponding alkanol which is, in turn, reacted with acryloyl chloride as described above to form an acrylate according to the following reaction scheme:

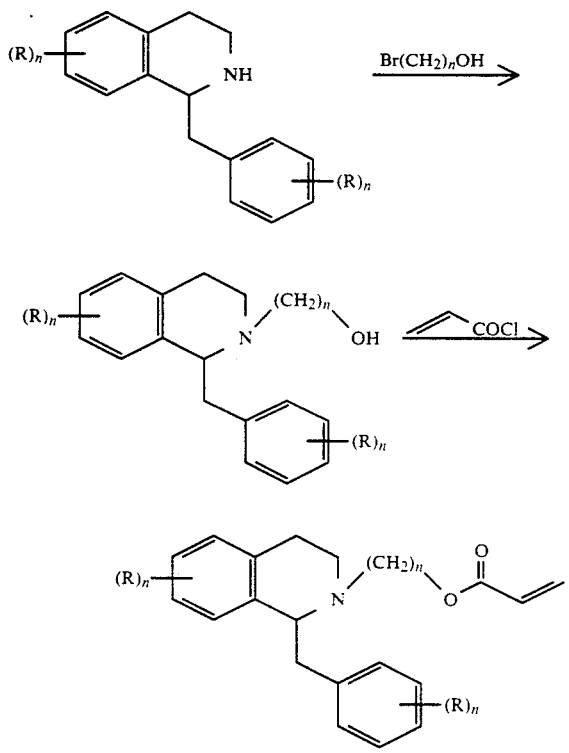

wherein n is 1 to 6.

The desired 1-benzyl-tetrahydroisoquinoline alkanol formed in the above reaction scheme may be reacted with a bromoacid represented by the formula BR-$(CH_2)_n$—COOH to form a compound represented by the formula

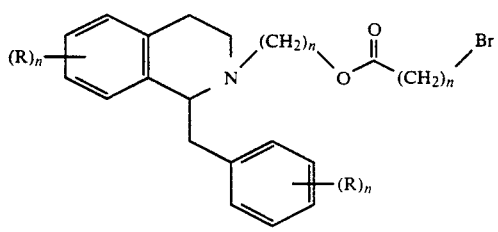

Either of the above intermediates, i.e. the bromo ester or the acrylate, is then reacted with an appropriate amine represented by the formula R'—$NH_2$, wherein R' is as defined above to form a bis-tetrahydroisoquinoline which is thereafter quaternized as described above.

The quaternization of the ring nitrogens in the subject compounds creates new asymmetric centers. Because the quaternization step lacks complete diastereoselectivity, the resultant compounds are mixtures of disastereomers. The subject invention, therefore, encompasses all optically active forms of the compounds, and combinations thereof as well as racemates and meso forms thereof. As there is an asymmetric center in the tetrahydroisoquinoline moieties on opposite ends of the bridge, and the geometric relation between the 1-benzyl group and the bridge may be independently cis or trans, the compounds may be all trans, all cis, cis-trans or trans-cis. Insofar as geometric relation of the subject compounds is concerned, the trans-trans relation is preferred.

It will be appreciated that the utilization of optically active 1-benzyl tetrahydroisoquinolines significantly reduces the number of potential diastereomers owing to fixed stereochemistry at the 1-position. Optically active tetrahydroisoquinolines are prepared by known procedures via resolution of the free-base with appropriate organic acid compounds, such as tartaric acid derivatives. Further reduction in the number of potential diastereoisomers is realized when the bridge nitrogen is symmetrical.

Patent publications such as Stenlake et al and El-Sayad et al, discussed under Background of the Invention, teach that the preferred direction of quaternization of tetrahydroisoquinolines is from the side opposite the 1-alkyl substituent. Wherein quaternization is effected with a methyl group, there is produced a compound wherein the geometric relationship of the 1-benzyl substituent to the bridge connection in the major isomer is cis. On the other hand, when an N-methyl tetrahydroisoquinoline is quaternized with a haloalkanol or other larger group, the predominate geometric relationship is trans. Typically, there is usually obtained a mixture of trans and cis isomers in a ratio of about 3:1 to about 5:1.

Previously, efforts to separate these isomers by fractional crystallization have not produced consistent results and have caused a significant loss of material. In accordance with the present invention, a method is provided whereby the cis and trans alkanol quats can be effectively separated by chromatography of their esters of mono-methyl biphenic acid or similar acids such as, for example, 2-phenyl benzoic acid, or their corresponding amides. The esters can be prepared by one of two syntheses.

In the first synthesis, as shown in the following scheme, the alkanol quaternary compound of an N-methyltetrahydroisoquinoline is reacted with the biphenic acid mono- methyl ester in the presence of an activating or coupling agent, such as dicyclohexylcarbodiimide. The diphenic acid monomethyl ester can be formed by conventional means such as by the reaction of the corresponding anhydride with methanol. The quaternary compound can likewise be formed conventionally by the reaction of an N-methyltetrahydroisoquinoline with a compound represented by the formula X—$CH_2$—$(CH_2)_n$—OH wherein X is a halogen and n is 1 to 3.

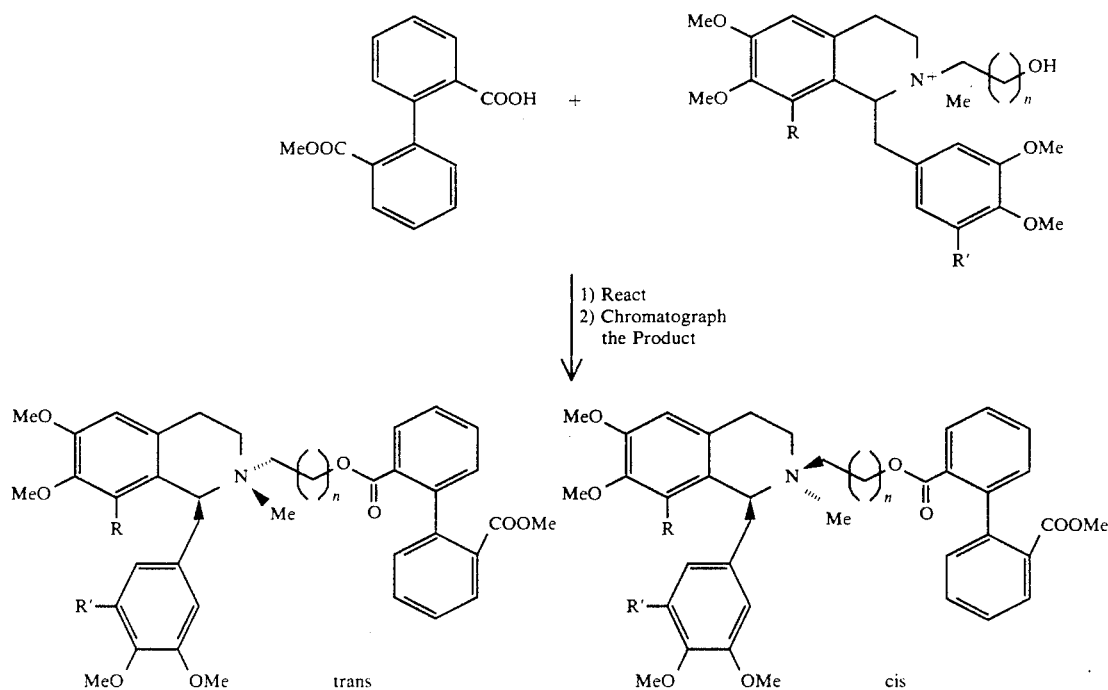

In the second synthesis, shown in the following scheme, the haloethyl ester of mono-methyl biphenic acid ester is initially formed and N-methyl tetrahydroisoquinoline directly quaternized therewith. Separation of the cis and trans isomers formed by either synthesis is readily carried out by chromatography, for example, on a silica gel column utilizing an eluent of methanol, ethyl acetate and trifluoroacetic acid. Other solvents which can be components of the eluent include other lower alkanols, such as ethanol and isopropanol, organic acids, such as acetic acid, and mineral acids, such as sulfuric acid. The isolated, purified esters are readily hydrolyzed, for example, using alcoholic base such as sodium hydroxide in ethanol.

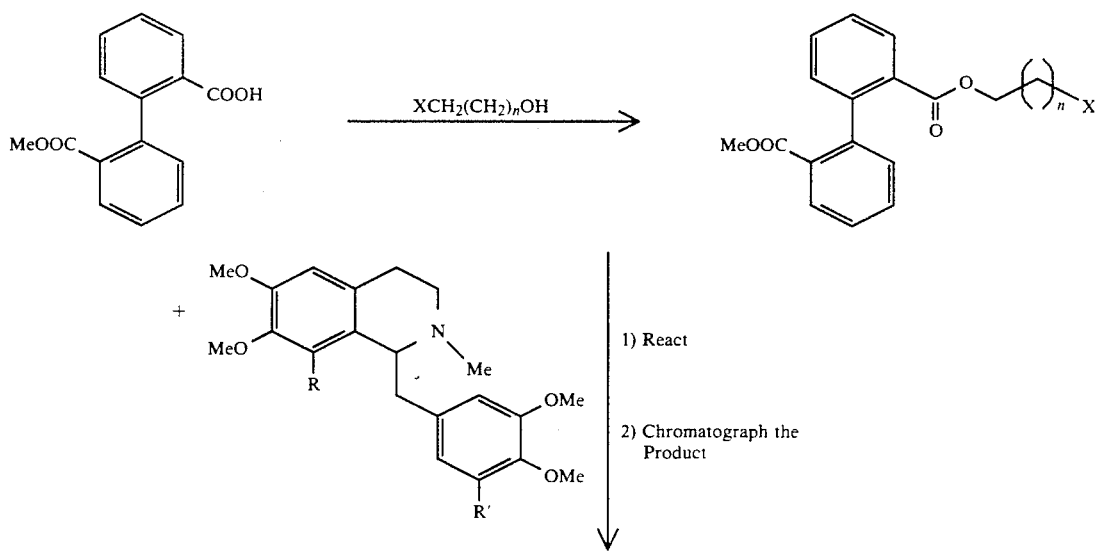

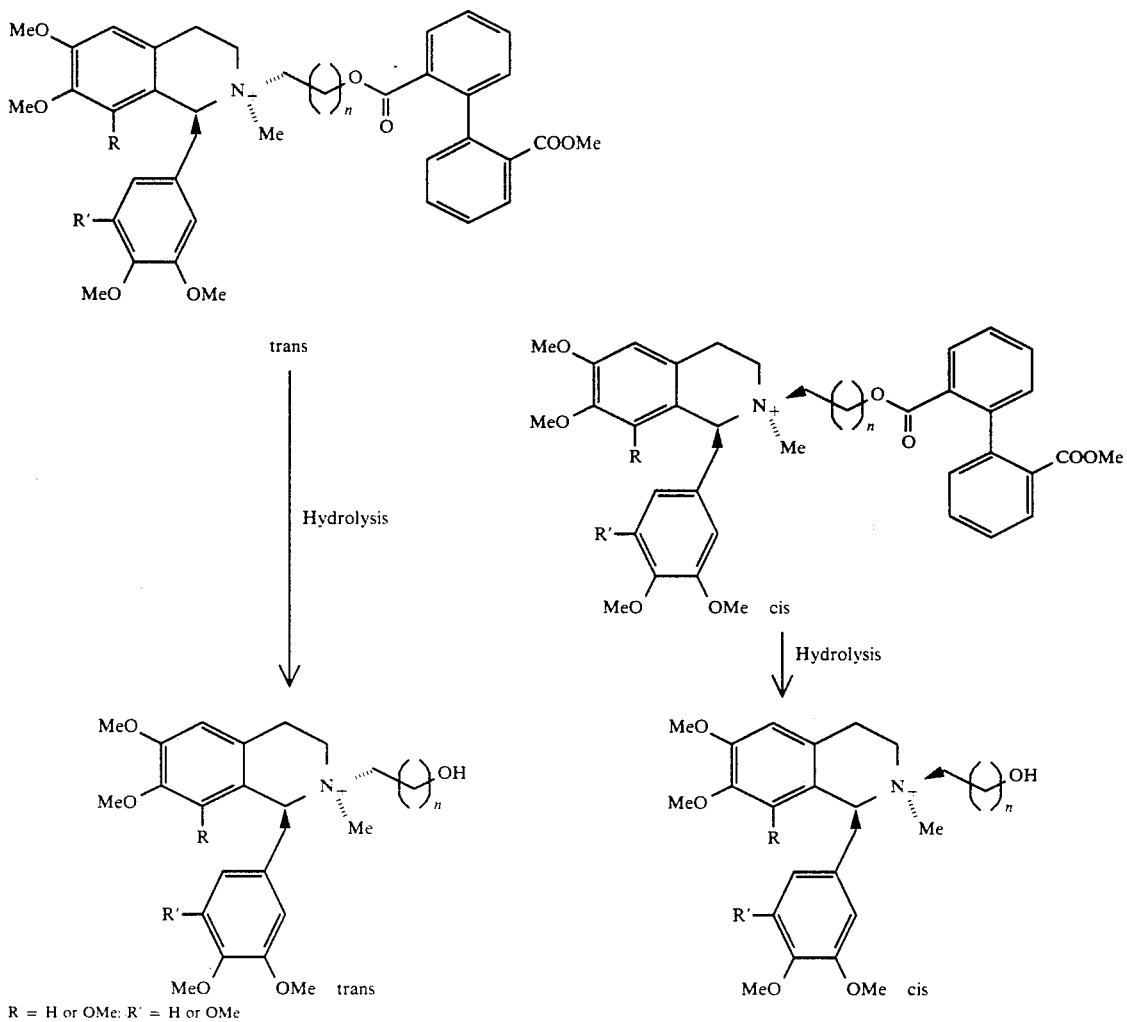

R = H or OMe; R' = H or OMe

As shown in the following scheme, coupling of either the cis or trans alkanol quaternary compounds with the amine diacid of the bridge moiety is readily carried out by conventional methods of coupling an alcohol and an acid as described previously. By this method, it is possible to control the stereochemistry at the 1-position of the tetrahydroisoquinoline moiety and at the quaternary nitrogen, the 2-position. Therefore, it is possible in accordance with the present invention to obtain a single isomer in purified form.

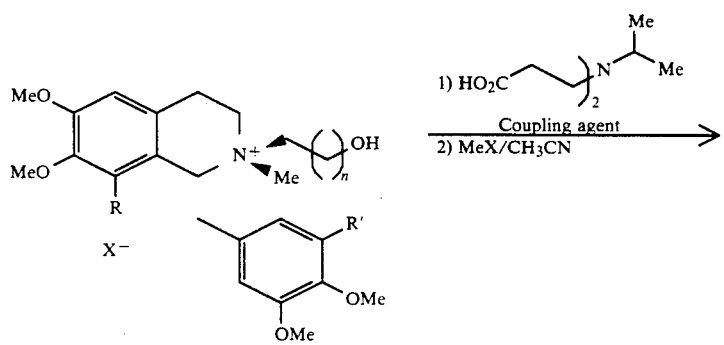

-continued

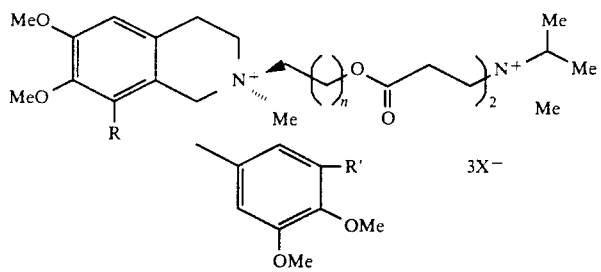

R = H or OMe
R' = H or OMe

The compounds of the present invention can be administered parenterally, i.e. by intravenous, intramuscular or subcutaneous administration. Suitable pharmaceutically carriers for compositions containing the subject compounds include, for example, isotonic water, sterile water for injection (USP), alone or in combination with other solubilizing agents such as ethanol, propylene glycol, or other conventional solubilizing agents known to those skilled in the art such as Emulphor ™, Cremophor-EL ™, and the like.

The sterile solutions or suspensions containing the subject compounds may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. A preferred preparation is an aqueous solution of the inventive compound buffered to a pH of about 4. The parenteral preparations may be dispensed in ampules, disposable syringes, or multiple dosage vials made of glass or plastic.

The compounds of the present invention can be administered to mammals, e.g., animals or humans, in amounts effective to provide the desired muscle relaxant therapeutic effect. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the dosage unit for a particular patient (man) can be as low as about one mg per kg of body weight, which the practitioner may titrate to the desired effect. It is advantageous to formulate the subject compositions in dosage unit forms for ease of administration and uniformity of dosage.

Typical parenteral compositions will contain at least about 0.1%, by weight, of the inventive compound, however, this amount may vary to between about 0.1% and 50%, by weight, of the inventive compound. The exact amount of the inventive compound present in such compositions is such that a suitable dosage unit level will be obtained. The compounds of the present invention are preferably administered intravenously and the initial dosage used will generally be in the range from about 1.35 mg to about 2.75 mg, preferably from about 1.95 mg per kg of patient body weight. This dosage is the typical dosage necessary for an intubation procedure, and is defined as the $ED_{90}$ dosage. After this initial dosage is administered, a smaller dosage is administered intravenously either by bolus or infusion to maintain muscle relaxation during the surgical procedure. The volume for the initial dosage administered intravenously will typically be from about 3 ml to about 7 ml and this dosage volume will be injected over a time period of from about 3 seconds to about 10 seconds.

The present invention is further illustrated by the following examples which are presented for purposes of demonstrating, but not limiting, the preparation of the compounds and compositions of this invention.

EXAMPLE 1

This Example illustrates the preparation of a bis-acrylate by reaction of an amine-diol with acryloylchloride.

Dihydroxyethyl-isopropylamine (15.06 g, 102.3 mmol) was combined with triethylamine (45.6 ml, 327.35 mmol) and 4-dimethylaminopyridine (1.26 g, 10.23 mmol) in dichloromethane (210 ml). The mixture was cooled, and a solution of acryloyl chloride (1.26 g, 102.23 mmol) in dichloromethane (75 ml) added thereto dropwise over 30 minutes. The mixture was allowed to warm to room temperature and stirring was continued over 21 hours. Water (125 ml) was added, stirring was continued for a further 10 minutes after which the mixture was extracted with ether (375 ml). The extract was dried over sodium sulfate and concentrated to produce an oil which was flash chromotographed on silica gel using hexane/ethyl acetate (97/3) as the elutent. After 6 liters of the elutent had been used, the polarity of the elutent was increased by changing the mixture to 90/10. There was obtained 16 g (62%) of isopropyl-di(acrylylethyl)amine as a clear oil.

EXAMPLE 2

This Example illustrates the preparation of a 1-benzyl-tetrahydroisoquinoline bis-amine.

Racemic tetrahydropapaverine oxalate (2.0 g, 4.61 mmol) was suspended in 30 ml of water and basified with ammonium hydroxide to a pH of about 9. The mixture was diluted with 100 ml of chloroform, stirred for 15 minutes, the layers separated, and the aqueous layer extracted with a further 100 ml of chloroform. The combined organic layers were dried over sodium sulfate and concentrated. The resulting free base was dissolved in 6.0 ml of p-xylene and combined with the isopropyl-bis-(acrylylethyl)amine formed in Example 1 (0.54 g, 2.10 mmol). The mixture was maintained with stirring at a temperature of 130° C. for 3 days. The solvent was then removed, and the crude reaction mixture flash chromotographed on silica gel with ethyl acetate to yield 1.15 g (55%) of pure isopropyl-di-2-[3-(N-tetrahydropapaverinyl)-proponyl]ethyl amine.

EXAMPLE 3

This Example illustrates the quaternizing of tertiary amines such as that formed in Example 2.

Isopropyl-bis-2-[3-(N-tetrahydropapaverinyl)-propionyl]ethylamine formed in Example 2 (1.15 g, 1.16 mmol) was dissolved in 15 ml of acetonitrle at room temperature An excess of methyl iodide (4.5 ml) was added as a single portion, and the mixture was stirred for 22 hours. The reaction mixture was then added dropwise to 250 ml of ether, and the resulting precipitate suction filtered on a Bachner funnel. The filter cake was washed with 200 ml of ether, placed under vacuum for 30 minutes, dissolved in 20 ml of methylene chloride and reprecipitated into 250 ml of ether. The precipitate was recovered, washed and dried under vacuum as before. The solid was dried in a vacuum oven for 16 hours at 65° C. to yield 1.37 g (81%) of isopropyl-methyl-bis-2-[3-(N-tetrahydropapaverinium)-propionyl] ethyl ammonium triiodide as an off-white solid, mp 142°–145° C., structure confirmed by NMR (270 MHZ, CDCl$_3$).

EXAMPLES 4-40

Compounds were prepared according to the procedures of Examples 1-3 having structures according to the general formula wherein n equals 2

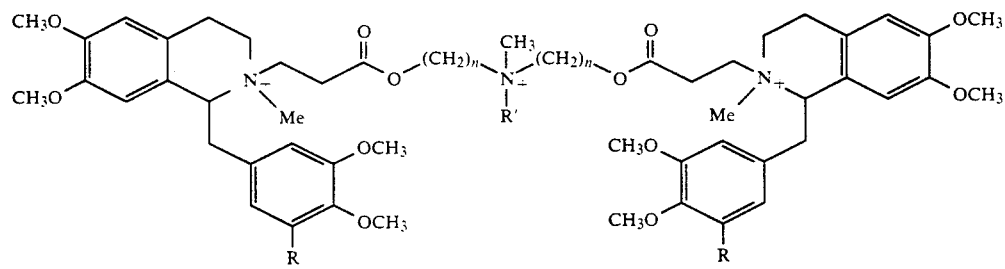

| Example | R | R' | Yield (%) | mp. (°C.) |
|---|---|---|---|---|
| 4 | OCH$_3$ | CH$_3$ | 82 | 141–155 |
| 5 | H | CH$_3$ | 83 | 132–145 |
| 6 | H | n-C$_4$H$_9$ | 78 | 134–138 |
| 7 | H | C$_2$H$_5$ | 83 | 127–136 |
| 8 | OCH$_3$ | n-C$_4$H$_9$ | 95 | 125–132 |
| 9 | OCH$_3$ | C$_2$H$_5$ | 90 | 120–133 |
| 10 | H | (CH$_2$)$_2$COOCH$_3$ | 83 | 121–144 |
| 11 | OCH$_3$ | (CH$_2$)$_2$COOCH$_3$ | 82 | 132–145 |
| 12 | H | i-C$_3$H$_7$ | 81 | 142–145 |
| 13 | OCH$_3$ | i-C$_3$H$_7$ | 75 | 142–145 |
| 14 | OCH$_3$ | (CH$_2$)$_2$—O—C(=O)—CH=CH$_2$ | 88 | 109–136 |
| 15 | H | (CH$_2$)$_2$—O—C(=O)—CH=CH$_2$ | 86 | 105–134 |
| 16 | OCH$_3$ | CH$_2$Ph | 96 | 77–99 |
| 17 | H | CH$_2$Ph | 74 | 70–92 |

The following compounds did not form a quaternary salt on the bridge nitrogen:

| Example | R | R' | Yield (%) | mp. (°C.) |
|---|---|---|---|---|
| 18 | H | t-C$_4$H$_9$ | 76 | 78–84 |
| 19 | OCH$_3$ | t-C$_4$H$_9$ | 83 | 129–133 |
| 20 | H | (CH$_2$)$_2$—O—C(=O)—CH$_3$ | 96 | 94–111 |
| 21 | H | (CH$_2$)$_2$—O—C(=O)—CH$_3$ | 86 | 91–108 |

The following compounds wherein the substituent on the bridge nitrogen is

also do not form a quaternary salt on the bridge nitrogen:

| Example | R | R' | Y | Yield (%) | mp. (°C.) |
|---|---|---|---|---|---|
| 22 | H | H | PhCH$_2$O | 96 | 120–140 |
| 23 | OCH$_3$ | H | PhCH$_2$O | 75 | 130–138 |
| 24 | OCH$_3$ | OCH$_3$ | PhCH$_2$O | 82 | 110–120 |
| 25 | H | H | H | 74 | 122–134 |
| 26 | OCH$_3$ | H | H | 73 | 116–122 |

The following compounds were prepared from optically active tetrahydroisoquinoline and, therefore, are optically active:

| Example | R | R' | Yield (%) | mp. (°C.) | [α]$_D$ |
|---|---|---|---|---|---|
| 27 | H | C$_2$H$_5$ | 73 | 140-142 | (+)55.2° (1.00, CHCl$_3$) |
| 28 | H | i-C$_3$H$_7$ | 70 | 142-143 | (+)58.9° (1.08, CHCl$_3$) |
| 29 | H | i-C$_3$H$_7$ | 90 | 142-143 | (−)58.1° (1.04, CHCl$_3$) |
| 30 | H | C$_2$H$_5$ | 89 | 141-142 | (−)59.3° (1.04, CHCl$_3$) |
| 31 | OCH$_3$ | i-C$_3$H$_7$ | 89 | 137-138 | (−)56.1° (1.32, CHCl$_3$) |
| 32 | OCH$_3$ | C$_2$H$_5$ | 88 | 136-137 | (−)56.1° (1.30, CHCl$_3$) |

The following compounds are illustrative of compounds represented by the formula first given above, wherein the meaning of n in the bridge is other than 2. These compounds are also optically active:

| Example | R | n | Configuration | Yield (%) | mp. (°C.) | [α]$_D$ |
|---|---|---|---|---|---|---|
| 33 | i-C$_3$H$_7$ | 3 | S | 93 | 142-150 | +58.5 |
| 34 | C$_2$H$_5$ | 3 | S | 93 | 139-145 | +56.3 |
| 35 | i-C$_3$H$_7$ | 1 | R | 92 | 138-146 | −56.4 |
| 36 | i-C$_3$H$_7$ | 1 | S | 92 | 134-138 | +56.1 |
| 37 | C$_2$H$_5$ | 1 | R | 91 | 134-136 | −45.3 |
| 38 | C$_2$H$_5$ | 1 | S | 80 | 130-132 | +55.0 |
| 39 | i-C$_3$H$_7$ | 4 | S | 69 | 100-102 | +54.0 |
| 40 | i-C$_3$H$_7$ | 5 | S | 70 | 115-118 | +58.1 |

EXAMPLE 41

This Example illustrates the preparation of a compound represented by the formula

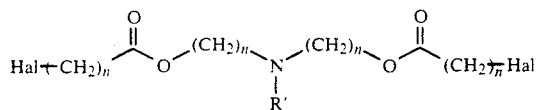

wherein Hal is bromine, n is 2, and R' is isopropyl.

In a suitable vessel, there was combined 4-bromobutyric acid (5.0 g, 0.03 mmol), 4-dimethylaminopyrdine (0.2 g) and dicyclohexylcarbodiimide (6.18 g, 0.03 mmol) in 25 ml of methylene chloride. To this mixture was added dropwise a solution of N-isopropyldiethanolamine (2.0 g, 0.015 mmol) in 10 ml of methylene chloride. The resulting exothermic mixture was stirred for 48 hours, filtered, concentrated, and the product purified by MPLC chromatography on silia gel utilizing an 80:20 mixture of hexane and ethyl acetate as the eluent. There was produced 3.6 g of isopropyl-di-[2-(3- bromopropionyl)-ethyl]-amine.

EXAMPLE 42

The free base of (+/−)-tetrahydropapaverine (1.50 g, 4.4 mmol) formed in accordance with Example 2, was combined with the tertiary amine prepared in Example 41 (0.93 g, 2.0 mmol) in 10 ml of acetonitrile. The resultant mixture was added dropwise to a solution of potassium carbonate (2.25 g, 16.3 mmol) in 40 ml of acetonitrile. The mixture was maintained at 50° C. for 16 hours, cooled to room temperature, combined with 15 ml of water, and extracted with two 100 ml portions of ether.

The combined ether extracts were washed with two 15 ml portions of water, dried over sodium sulfate and concentrated. Purification by MPLC chromatography on silica gel with ethyl acetate produced 1.10 g of pure isopropyl-di-2-[3-(N-tetrahydropapverinyl)-proponyl]-ethyl amine and 0.80 g of mixed fractions. The purified product was quaternized in accordance with the procedure of Example 3.

EXAMPLE 43

This Example illustrates the preparation of compounds of the invention by the formation of a 1-benzyl-tetrahydroisoquinoline-alkanol.

The free base of (+/−)-tetrahydropapaverine (2.70 g, 7.86 mmol) formed in accordance with Example 2, was combined with potassium carbonate (4.35 g, 31.45 mmol) and of 2-bromopropanol (1.47 g, 11.79 mmol) in 20 ml of acetonitrile. The mixture was heated at 50° C. for 48 hours, cooled to room temperature, and the potassium carbonate filtered off. The filtrate was diluted with 100 ml of ether, washed with 20 ml of water, dried over sodium sulfate and concentrated. Chromatography yielded 2.30 g of 2-(1-hydroxyethyl)-tetrahydropapaverine.

EXAMPLE 44

In a suitable vessel was combined the alkanol formed in Example 43 (2.30 g, 5.94 mmol), triethylamine (0.96 g, 9.50 mmol) and 4-dimethylamino-pyridine (catalytic) in 15 ml of methylene chloride. The mixture was cooled in an ice bath and treated dropwise with acryloyl chloride (0.60 g, 6.25 mmol) in 5 ml of methylene chloride. The mixture was allowed to warm to room temperature and stirred for 21 hours thereafter. The reaction mixture was combined with 5 ml of water, extracted with two 30 ml portions of ether, dried and concentrated. Chromatographic purification on silica gel produced 1.00 g of 2-(1-acryloylethyl)-tetrahydropapaverine.

The acrylate produced above (1.50 g, 3.40 mmol) was combined with excess isopropylamine (5.00 ml, 58.70 mmol) and allowed to stir neat at room temperature for IB hours. The excess isopropylamine was removed under vacuum. Another equivalent (1.50 g, 3.40 mmol) of the above acrylate was added. Methylene chloride (5.00 ml) was added to produce a homogeneous solution. The methylene chloride was then evaporated, and the resulting viscous residue heated neat at 95° -98° C. for 5 days. Chromatography on silica gel with ethyl acetate afforded 1.50 g of isopropyl-di-2-[3-(N-tetrahydropapaverinyl)propionyl]ethyl amine which was then quaternized in accordance with the procedure of Example 3 utilizing methyl bromide to yield N,N'-dimethyl-N,N'-3,11-dioxa-4,10-dioxo-7-isopropyl-7-methyl-7-azoniatridecylene-1,13-bis-tetrahydropapaverinium tribromide, mp 142°-144° C., yield 86%.

EXAMPLE 45

Diphenic anhydride (10 g, 0.045 mol) was dissolved in 30 ml of methanol and refluxed overnight. Removal of the solvent and drying the product under vacuum afforded 11.8 g of diphenic acid momo-methyl ester.

Laudanosine, 2-methyl-tetrahydropapaverine, (10 g, 0.46 mol) and sodium iodide (7.24 g, 0.049 mol) were dissolved in 250 ml of acetone. To this solution was added bromoethanol (6.09 g, 0.048 mol) and the mixture was refluxed for 4B hours. Precipitation with ether afforded 24.39 g of a 3:1 trans-cis mixture of [2-methyl-2-(2-hydroxyethyl)]-tetrahydropapaverinium iodide.

Equimolar (0.0083 mol) amounts of the ester and iodide products formed above and 50 mg. of 4-dimethylaminopyridine were dissolved in 15 ml of methylene chloride. Dicyclohexylcarbodiimide (1.88 g, 0.009 mol) was added and the mixture stirred at room temperature for twelve hours. The reaction mixture was filtered and the precipitate was washed with methylene chloride. The filtrate was concentrated to afford a crude mixture of cis and trans 2-methyl-2-ethoxy-[(2-oxo-2'-carboxymethyl)-bisphenyl]tetrahydropapaveriniumiodide. The product was separated by chromatography on silica gel using a 70/30/0.6 mixture of ethyl acetate, methanol and trifluoroacetic acid. Following concentration of the chromatography fractions, the residues were individually dissolved in methylene chloride and the residual trifluoroacetic acid was neutralized with aqueous sodium bicarbonate. There was afforded 0.26 g of the cis ester and 2.14 g of the trans ester.

The trans ester (9.82 g) was dissolved in 20 ml of methanol. A solution of 10% by weight of sodium hydroxide in 70% aqueous ethanol was added dropwise until the solution turned light pink to phenophthalien end point. After fifteen minutes of stirring at room temperature, the product was recovered and purified by chromatography to yield 3.5 g of trans [2-methyl-2-(2-hydroxyethyl)]tetrahydropapaverinium iodide.

An analogous reaction and purification were carried out for the cis ester.

EXAMPLE 46

The hydrochloride salt of isopropyl-bis-(2-carboxylethyl)amine (250 mg., 0.0011 mol) was dissolved in 10 ml of methylene chloride and combined with N-methylmorpholine (0.12 ml, 0.0011 mol) and pentafluorophenol (408 mg., 0.0022 mol). Dicyclohexylcarbodiimide (454 mg., 0.0022 mol) and a catalytic amount of 4-dimethylaminopyridine were added and the mixture was stirred at room temperature overnight, then at 60 degrees for twenty four hours. The product, N,N'-dimethyl-N,N'-3,11-dioxa-4,10-dioxo-7-isopropylamino-tridecylene-1,13-bis-tetrahydropapaverinium diiodide, was separated by chromatography using a 62/38/0.06 mixture of methanol, ethyl acetate and trifluoroacetic acid. The trans-trans product (0.16 g) was quaternized with methyl iodide (1 ml) in acetonitrile (0.5 ml) at room temperature overnight. The product was precipitated with ether and purified to afford 0.13 g. of trans-trans N,N'-dimethyl-N,N'-3,11-dioxa-4,10-dioxo-7-isopropyl-7-methyl-7-azoniatridecylene-1,13-bis-tetrahydropapaverinium triiodide.

EXAMPLE 47

The following bioassay methodologies were used to demonstrate the neuromuscular junction blocking activity of the compounds of the invention. The relaxant properties of compounds with this pharmacologic mechanism could be used during surgical anesthesia to facilitate endotracheal intubation and retraction of muscle groups as required to expedite access to various body cavities. Each of these tests extended the knowledge of the clinical potential of the subject compounds. In instances where the compounds of this invention were not subjected to analysis in a specific test, it is possible to estimate such activity based on known relationships to other clinically available drugs which have been tested.

The first step, in mice, establishes a preliminary estimate of the potency and efficacy of the compounds. The animals were placed on a screen, inclined 45° to the horizontal. Effective doses caused the mice to lose their grip and slide down the inclined screen. The dose in mg/kg of body weight required to inhibit grip strength in 100% of the mice tested in a dosage group is reported.

The type of muscle relaxation produced by the test compounds was then determined by injection into chicks. Compounds which cause competitive blockage of post-synaptic acetylcholine receptors, i.e. nondepolarizing drugs, produce a flaccid paralysis in the chicks whereas drugs which cause depolarization of the post-synaptic muscle membrane produce a rigid paralysis. Only those compounds shown by this test to be nondepolarizing are tested further. This test established that the subject compounds are nondepolarizing muscle relaxants.

The rabbit paw twitch analysis was used to demonstrate the rate of onset and duration and to confirm the range of potency of test compounds. The mechanism of action was also confirmed in this test by observing train-of-four and tetanus fade, post-tetanic potentiation of single twitches and administration of the anticholinesterase drug neostigmine which reverses the relaxation. Reversibility, rapid onset and short duration are important factors to the anesthesiologist.

In Table I, the doses of the compounds of the invention are shown relative to doses of clinically available drugs. Clinically, 0.1 to 0.14 mg/kg of vecuronium has been used for endotracheal intubation, while 0.010 mg/kg is used for maintenance of relaxation. Therefore, as an estimate of the range of possible dosages which might be employed for the subject compounds, the ED90 would be doubled as an estimate for an intubating dose, while a dose 20 to 25% of the ED90 dose might be required for maintenance bolus doses. The clinical dose range might be between 29% to 200% of the estimated ED90.

TABLE I

| Neuromuscular Junction Blocking Activity (ED90 in mg/kg) | | |
| --- | --- | --- |
| Drug | Mouse | Rabbit |
| pancuronium | 0.020 | 0.012 |
| vercuronium | 0.025 | 0.017 |
| atracurium | 0.631 | 0.071 |
| succinyl choline | 0.200 | 0.129 |
| Example 7 | 1.259 | 1.884 |
| Example 9 | 0.794 | 1.782 |
| Example 12 | 1.259 | 2.360 |
| Example 13 | 0.501 | 2.474 |
| Example 23 | 1.585 | 0.532 |
| Example 26 | 1.000 | 1.709 |
| Example 27 | 1.585 | 2.660 |
| Example 28 | 1.585 | 2.190 |
| Example 29 | 1.995 | 2.000 |
| Example 30 | 5.012 | 1.700 |
| Example 31 | 6.310 | 2.930 |
| Example 32 | 5.012 | 3.760 |
| Example 44 | 1.000 | 1.858 |

The detailed pharmacologies in rabbits of the subject compounds are presented in Table II. The following is a brief description of the methodologies used in rabbits to describe neuromuscular blocking activity of the subject compounds. A more detailed description of these methods is presented in "Microcomputer Use in Measuring Onset, Duration, and Recovery from Non-Depolarizing Skeletal Muscle Relaxants in Rabbits", P.D. Thut et al., *Drug development Research* 5:182, 1985.

Male New Zealand white rabbits weighing between 2.5 and 3.4 kg were anesthetized with pentobarbital (30 mg/kg) and placed on their backs upon a 40° C. water filled temperature regulation pad. Following tracheostomy, the lungs were mechanically ventilated at 28 breaths per minute with room air, using an open system delivering 200 mi/stroke. This ventilation maintained $pCO_2$ at 38 mmHG and $pO_2$ at 85 mmHg. Direct arterial blood pressure was measured from the right common carotid artery. The test compounds were administered through a canula placed in the marginal ear vein. Each foreleg was taped to a cushioned plate held in a femur clamp attached to the spinal board rack. The left central digit of each paw was connected to a force displacement transducer for measurement of muscle tension. Nerve stimulation was provided by pairs of pin electrodes placed on both sides of the ulnar nerve at the elbow of both forearms. The right ulnar nerve was stimulated at Hz, 1 pps for 0.5 msec duration. The left ulnar nerve was similarly stimulated, every 15 seconds, with addition of interspersed trains-of-four and tetanizing stimuli. The parameters reported in Table II are: potency (ED90), which is the dose required to depress twitch tension to 10% of its control value; onset (T85%), which is the time from injection unit 85% of the maximal drug effect is achieved; duration, which is the time from injection until the train-of-four has recovered to 75%; blood pressure (BP), which is the percentage change of pre-drug blood pressure; and heart rate (HR), which is the percentage change from pre-drug heart rate.

TABLE II

| Rabbit Paw Twitch Equi-efficacious Dose Data | | | | |
|---|---|---|---|---|
| Compound | ED90 (mg/ kg) | T 85% (seconds) | Duration (minutes) | BP (% change) | HR (% change) |
| atracurium | 0.050 | 72.00 | 13.00 | −3.40 | −1.00 |
| vecuronium | 0.020 | 97.30 | 16.80 | 1.10 | −1.90 |
| pancuronium | 0.020 | 147.50 | 32.50 | 2.70 | 0.00 |
| succinyl choline | 0.129 | 44.00 | 13.60 | 26.50 | 31.80 |
| Example 7 | 1.884 | 34.16 | 6.22 | 3.40 | 1.40 |
| Example 9 | 1.782 | 31.48 | 9.54 | −3.10 | −1.00 |
| Example 12 | 2.360 | 29.88 | 8.87 | −3.00 | −0.90 |
| Example 13 | 2.474 | 34.40 | 9.10 | 4.90 | −1.10 |
| Example 23 | 0.532 | 34.00 | 8.10 | 0.00 | −3.00 |
| Example 26 | 1.709 | 37.58 | 9.41 | 0.80 | −2.30 |
| Example 27 | 2.663 | 34.96 | 8.76 | 0.70 | −1.10 |
| Example 28 | 2.190 | 45.87 | 8.25 | 6.40 | 0.50 |
| Example 29 | 1.998 | 41.26 | 7.74 | −3.90 | −0.10 |
| Example 30 | 1.703 | 29.44 | 7.22 | −3.30 | −4.60 |
| Example 31 | 2.928 | 40.09 | 8.48 | −4.70 | −3.10 |
| Example 32 | 3.761 | 40.71 | 6.92 | −3.40 | −3.30 |
| Example 44 | 1.858 | 28.50 | 6.80 | −1.30 | −1.40 |

Male beagle dogs weighing between 10 and 13 Kg were anesthetized with 3.6 MAC (minimum alveolar concentration) of 5 percent isoflurane in oxygen, via face mask to a level sufficient for endotracheal intubation to be performed. Once the animal had been intubated, the isoflurane was reduced to 1.75 MAC with an oxygen flow rate of 500 ml per minute.

The animals were ventilated with a constant flow ventilator (Ohmeda 7000) at a respiratory rate of 15 breaths per minute. Surgery was performed to isolate the right and left femoral artery and vien and the left-common caroid artery. The anesthesia level was thereafter reduced to 1.5 MAC and the vessels were catheterized. By suitable monitoring equipment, the animals' temperature, right atrial pressure, cardiac output, pulmonary artery pressure, intraventricular pressure and its rate of change were monitored.

Each animal's foreleg was bent at the elbow and secured to a restraint. The central digit was connected to a force displacement transducer for measurement of muscle tension. Nerve stimulation was provided by pairs of electrodes placed subcutaneously on both sides of the ulnar nerve in the elbow. Once calibration stimulation current level is determined, trains-of-four stimuli were given every twenty seconds throughout the experiment. The animals were allowed to stabilize over at least thirty minutes before introduction of test compound. The parameters measured were the same as determined in the Rabbit Paw Twitch experiment described above and are reported in Table III.

TABLE III

| Dog Paw Twitch Equi-efficacious Dose Data | | | | |
|---|---|---|---|---|
| Compound | ED90 (mg/ kg) | T 85% (seconds) | Duration (minutes) | HR (% change) | BP (% change) |
| atracurium | 0.079 | 164.80 | 25.60 | 3.00 | −1.10 |
| vecuronium | 0.019 | 171.00 | 26.62 | 3.50 | 2.30 |
| pancuronium | 0.010 | 169.00 | 45.70 | 0.20 | −1.80 |
| succinyl choline | 0.040 | 98.00 | 8.00 | 25.00 | 34.00 |
| Example 7 | 0.845 | 63.42 | 14.57 | −0.10 | −1.20 |
| Example 9 | 0.662 | 88.29 | 13.51 | 0.40 | −1.20 |
| Example 12 | 0.843 | 68.30 | 12.50 | 1.30 | 0.60 |
| Example 13 | 0.694 | 72.70 | 11.38 | 0.00 | 0.40 |
| Example 23 | 0.388 | 96.80 | 13.20 | 2.20 | 0.40 |
| Example 26 | 1.206 | 89.20 | 20.18 | 1.40 | 0.80 |
| Example 27 | 0.734 | 69.74 | 13.19 | −1.00 | 0.30 |
| Example 28 | 0.782 | 88.64 | 15.80 | −0.50 | 2.60 |
| Example 29 | 0 783 | 76.96 | 13.50 | 0.00 | 0.70 |
| Example 30 | 0.581 | 83.75 | 12.49 | −0.60 | −0.10 |
| Example 31 | 1.369 | 74.69 | 12.70 | −3.40 | 1.50 |
| Example 32 | 1.354 | 70.85 | 12.94 | −0.50 | 1.30 |
| Example 44 | 1.133 | 73.20 | 14.80 | 0.80 | −5.30 |

The results in the Tables show that the subject compounds, while not as potent as those used for comparison, are advantageous in that they possess a significantly faster onset of activity, shorter duration of activity and good cardiovascular profiles.

I claim:

1. A compound selected from those represented by the formula

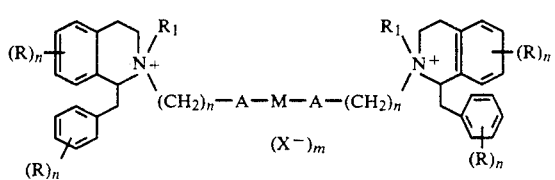

wherein:
A is

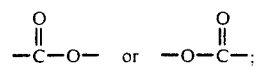

R is a $C_{1-3}$ alkoxy group or a methylenedioxy group;
$R_1$ is lower alkyl;
M is $-(CH_2)_n-Z-(CH_2)_n-$ Z is selected from the group consisting of —N+(R₂R₃)—, —N(R₄)—,

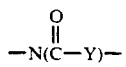

and —N[(CH₂)ₙ—A—R₅]—;

R₂ and R₃ are independently selected from the group consisting of: lower alkyl wherein one of the carbon atoms within the chain may be replaced by a heteroatom selected from the group consisting of N, S, and O; lower cycloalkyl; lower cycloalkyl lower alkyl; aryl; and aryl lower alkyl;

R₄ is a straight- or branched-chain $C_{1-10}$ alkyl group wherein one or more of the carbon atoms within the chain may be replaced by a heteroatom selected from the group consisting of N, S, and O; a substituted or unsubstituted lower cycloalkyl group; a substituted or unsubstituted lower cycloalkyl lower alkyl group; a substituted or unsubstituted aryl group, and

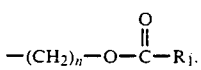

wherein the substituents are selected from the group consisting of lower-alkyl, halogenated lower-alkyl, lower-alkoxy, halogen, oxo, hydroxy, and acyloxy;

R₅ is lower alkyl or lower alkenyl;

Y is hydrogen, lower alkyl wherein one or more of the carbon atoms within the chain may be replaced by a heteroatom selected from the group consisting of N, S, and O; lower alkoxy; aryl; aryloxy; lower cycloalkyl; lower cycloalkyl lower alkyl; or —NR₂R₃;

X is a pharmaceutically acceptable anion;

m is 2 or 3;

n is independently 1 to 6;

and optically active forms thereof, meso forms thereof, cis-trans isomeric forms thereof and racemates thereof.

2. A compound in accordance with claim 1, where Z is —N(R₂R₃), R is methoxy, R₁ is methyl, n is two in the tetrahydroisoquinoline rings and 2 or 3 in the benzyl ring, and m is 3.

3. A compound in accordance with claim 1, wherein the geometric relationship between the 1-benzyl group on the tetrahydroisoquinoline rings and the —(CH₂)ₙ—A—M—A—(CH₂)ₙ— moiety is trans-trans.

4. A compound in accordance with claim 1, wherein R is methoxy, R₁ is methyl, one of R₂ and R₃ is lower alkyl, n is two in the tetrahydroisoquinoline rings and two or three in the benzyl rings, m is two, and Z is —N(R₄)— and R₄ is lower alkyl or

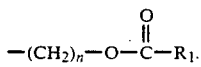

5. A compound in accordance with claim 4, wherein R₄ is t-butyl or 2-acetoxyethyl.

6. A compound in accordance with claim 1, wherein Z is

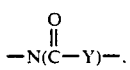

wherein Y is selected from the group consisting of aryloxy, alkoxy, and hydrogen.

7. A compound in accordance with claim 1, wherein said pharmaceutically acceptable anion is selected from the group consisting of bromide, chloride, and besylate.

8. A compound in accordance with claim 1, wherein said compound is N,N'-dimethyl-N,N'-3,11-dioxa-4,10-dioxo-7-isopropyl-7-methyl-7-azoniatridecylene-1,13-bis-tetrahydropapaverinium tribromide.

9. A compound in accordance with claim 1, wherein said compound is N,N'-dimethyl-N,N'-4,10-dioxa-3,11-dioxo-7-isopropyl-7-methyl-7-azoniatridecylene-1,13-bis-tetrahydropapaverinium tribromide.

10. A compound in accordance with claim 1, wherein said compound is N,N'-dimethyl-N,N'-4,10-dioxa-3,11-dioxo-7-isopropyl-7-methyl-7-azoniatridecylene-1,13-bis[1',2',3',4'-tetrahydro -6',7'-dimethoxy-1-(3'',4'',5''-trimethoxybenzyl)isoquinolinium] tribromide.

11. A compound in accordance with claim 1, wherein said compound is N,N'-dimethyl-N,N'-3,11-dioxa-4,10-dioxo-7-isopropyl-7-methyl-7-azoniatridecylene -1,13-bis[1',2',3',4'-tetrahydro-6',7'-dimethoxy-1-(3'',4'',5''-trimethoxybenzyl)isoquinolinium] tribromide.

12. A compound in accordance with claim 1, wherein said compound is N,N'-dimethyl-N,N'-4,12-dioxa-5,11-dioxo-8-isopropyl-8-methyl-8-azoniapentadecylene -1,15-bis-tetrahydropapaverinium tribromide.

13. A compound in accordance with claim 1, wherein said compound is N,N'-dimethyl-N,N'-4,12-dioxa-5,11-dioxo-8-isopropyl-8-methyl-8-azoniapentadecylene -1,15-bis-[1',2',3',4'-tetrahydro-6',7'-dimethoxy-1-(3'',4'',5''-trimethoxybenzyl)isoquinolinium] tribromide.

14. A muscle-relaxant composition comprising a nontoxic, pharmaceutically acceptable carrier and a therapeutically effective amount of a compound represented by the formula

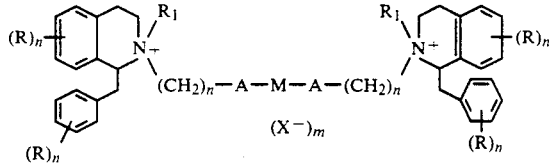

wherein:

A is

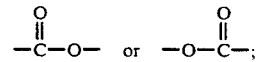

R is a $C_{1-3}$ alkoxy group or a methylenedioxy group;

R₁ is lower alkyl;

M is —(CH₂)ₙ—Z—(CH₂)ₙ—;

Z is selected from the group consisting of —N+(R₂R₃)—, —N(R₄)—,

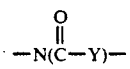

and —N[(CH₂)ₙ—A—R₅]—;

R₂ and R₃ are independently selected from the group consisting of: lower alkyl wherein one of the carbon atoms within the chain may be replaced by a heteroatom selected from the group consisting of N, S, and O; lower cycloalkyl; lower cycloalkyl lower alkyl; aryl; and aryl lower alkyl;

$R_4$ is a straight- or branched-chain $C_{1-10}$ alkyl group wherein one or more of the carbon atoms within the chain may be replaced by a heteroatom selected from the group consisting of N, S, and O; a substituted or unsubstituted lower cycloalkyl group; a substituted or unsubstituted lower cycloalkyl lower alkyl group; a substituted or unsubstituted aryl group, and

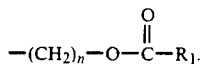

wherein the substituents are selected from the group consisting of lower-alkyl, halogenated lower-alkyl, lower-alkoxy, halogen, oxo, hydroxy, and acyloxy;

$R_5$ is lower alkyl or lower alkenyl;

Y is hydrogen, lower alkyl wherein one or more of the carbon atoms within the chain may be replaced by a heteroatom selected from the group consisting of N, S, and O; lower alkoxy; aryl; aryloxy; lower cycloalkyl; lower cycloalkyl lower alkyl; or —$NR_2R_3$;

$X^-$ is a pharmaceutically acceptable anion;

m is 2 or 3;

n is independently 1 to 6;

and optically active forms thereof, meso forms thereof, cis-trans isomeric forms thereof and racemates thereof.

15. A method of producing muscle relaxation in a mammal in need thereof comprising administering to the mammal a muscle relaxant effective amount of a compound represented by the formula

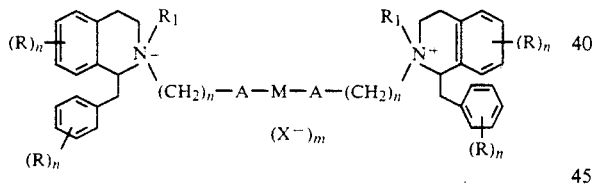

wherein:

A is

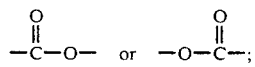

R is a $C_{1-3}$ alkoxy group or a methylenedioxy group;

$R_1$ is lower alkyl;

M is —$(CH_2)_n$—Z—$(CH_2)_n$—;

Z is selected from the group consisting of —$N^+(R_2R_3)$—, —$N(R_4)$—,

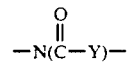

and —$N[(CH_2)_n$—A—$R_5]$—;

$R_2$ and $R_3$ are independently selected from the group consisting of: lower alkyl wherein one of the carbon atoms within the chain may be replaced by a heteroatom selected from the group consisting of N, S, and O; lower cycloalkyl; lower cycloalkyl lower alkyl; aryl; and aryl lower alkyl;

$R_4$ is a straight- or branched-chain $C_{1-10}$ alkyl group wherein one or more of the carbon atoms within the chain may be replaced by a hetero- atom selected from the group consisting of N, S, and O; a substituted or unsubstituted lower cycloalkyl group; a substituted or unsubstituted lower cycloalkyl lower alkyl group; a substituted or unsubstituted aryl group; and

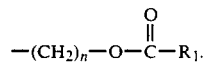

wherein the substituents are selected from the group consisting of lower-alkyl, halogenated lower-alkyl, lower-alkoxy, halogen, oxo, hydroxy, and acyloxy;

$R_5$ is lower alkyl or lower alkenyl;

Y is hydrogen, lower alkyl wherein one or more of the carbon atoms within the chain may be replaced by a heteroatom selected from the group consisting of N, S, and O; lower alkoxy; aryl; aryloxy; lower cycloalkyl; lower cycloalkyl lower alkyl; or —$NR_2R_3$;

$X^-$ is a pharmaceutically acceptable anion;

m is 2 or 3;

n is independently 1 to 6;

and optically active forms thereof, meso forms thereof, cis-trans isomeric forms thereof and racemates thereof.

16. A method of producing muscle relaxation in accordance with claim 15, wherein said compound is N,N'-dimethyl-N,N'-3,11-dioxa-4,10-dioxo-7-isopropyl-7-methyl-7-azoniatridecylene-1,13-bis-tetrahydropapaverinium tribromide.

17. A method of producing muscle relaxation in accordance with claim 15, wherein said compound is N,N'-dimethyl-N,N'-4,10-dioxa-3,11-dioxo-7-isopropyl-7-methyl-7-azoniatridecylene-1,13-bis-tetrahydropapaverinium tribromide.

* * * * *